United States Patent [19]

Uick

[11] Patent Number: 5,716,602
[45] Date of Patent: Feb. 10, 1998

[54] INSECT REPELLENT SUNSCREEN

[75] Inventor: Heidi J. Uick, Racine, Wis.

[73] Assignee: S. C. Johnson & Sons, Inc., Racine, Wis.

[21] Appl. No.: 670,944

[22] Filed: Jun. 26, 1996

[51] Int. Cl.$^6$ .............. A61K 7/42; A61K 31/19; A61K 31/165; A01W 25/00
[52] U.S. Cl. .............. 424/59; 424/60; 424/78.02; 424/400; 424/403; 512/1; 514/557; 514/617
[58] Field of Search .............. 424/59, 60, 78.02, 424/403; 512/1; 514/557, 617

[56] References Cited

U.S. PATENT DOCUMENTS

| | | |
|---|---|---|
| 1,471,344 | 10/1923 | Loudin . |
| 2,435,005 | 1/1948 | Huppke et al. . |
| 3,186,912 | 6/1965 | Beamer . |
| 3,594,481 | 7/1971 | Lindberg et al. . |
| 3,918,612 | 11/1975 | Voulgaris . |
| 4,083,966 | 4/1978 | Bowell . |
| 4,322,400 | 3/1982 | Yuhas . |
| 4,335,104 | 6/1982 | VanCleave . |
| 4,389,418 | 6/1983 | Burton . |
| 4,457,910 | 7/1984 | Van Cleave . |
| 4,477,467 | 10/1984 | Nishizawa et al. . |
| 4,529,598 | 7/1985 | Wong . |
| 4,537,762 | 8/1985 | Fogel et al. . |
| 4,559,226 | 12/1985 | Fogel et al. . |
| 4,740,369 | 4/1988 | Phalangas et al. . |
| 4,810,489 | 3/1989 | Murray et al. . |
| 4,895,727 | 1/1990 | Allen . |
| 5,116,604 | 5/1992 | Fogel et al. . |
| 5,120,816 | 6/1992 | Gould et al. . |
| 5,204,090 | 4/1993 | Han . |
| 5,208,011 | 5/1993 | Vaughan . |
| 5,227,406 | 7/1993 | Beldock et al. . |
| 5,334,691 | 8/1994 | Gould et al. . |
| 5,346,922 | 9/1994 | Beldock et al. . |
| 5,476,643 | 12/1995 | Fogel . |
| 5,476,648 | 12/1995 | Fogel . |
| 5,486,352 | 1/1996 | Guerrero . |
| 5,518,712 | 5/1996 | Stewart . |

FOREIGN PATENT DOCUMENTS

| | | |
|---|---|---|
| 036138 | 9/1981 | European Pat. Off. . |
| WO 88/01164 | 2/1988 | WIPO . |
| WO 94/00104 | 1/1994 | WIPO . |
| WO 95/19161 | 7/1995 | WIPO . |

OTHER PUBLICATIONS

ELEFAC I–205, Bernel Chemical Company, Inc., First Edition Jan. 1, 1993.

Primary Examiner—Shelley A. Dodson

[57] ABSTRACT

Disclosed herein are sunscreens. They are formulated to also include a water resistance agent and an insect repellent. One form has in an aqueous emulsion DEET, a sunscreen agent, an anionic surfactant, an alkylated PVP, and octyldodecyl neopentanoate. Methods for making and using such sunscreens are also disclosed.

17 Claims, No Drawings

INSECT REPELLENT SUNSCREEN

TECHNICAL FIELD

The present invention relates to compositions that provide high SPF levels of sunscreen protection with superior insect repellency capability. They do so in environments where skin is regularly exposed to water.

BACKGROUND ART

The sun's ultraviolet rays tan human skin. However, there are adverse affects of prolonged exposure to such ultraviolet rays, such as drying, sunburn, and in extreme cases skin cancer. Thus, the art has developed sunscreen preparations, including lotions and other materials that can be applied to the skin to help screen-out or otherwise reduce the harmful effects of the ultraviolet rays of the sun.

It also is often desirable to also have protection outdoors against annoyance by mosquitoes and other flying pests. This can be achieved by separately applying an insect repellent to the skin. However, this requires two separate applications and two separate products, and runs the risk that the ingredients of the sunscreen and repellent will not be fully compatible.

There have therefore been attempts to provide a single lotion which provides sunscreen protection and insect repellent protection. See e.g. PCT application WO 95/19161 (1995) and U.S. Pat. Nos. 5,518,712; 5,346,922; 3,186,912; and 1,471,344. The disclosure of these items and of all other publications referred to herein are incorporated by reference as if fully set forth herein.

A factor that further complicates matters is the desirability for such protectants to continue to be effective even after the user has been in water, e.g. after swimming at a beach. Thus, water resistance compounds have been added to some of these products. See e.g. PCT application WO 95/19161 (1995) and U.S. Pat. Nos. 5,518,712 and 4,810,489.

However, when seeking high SPF protection, e.g. equal to or greater than SPF 15, and good water resistance characteristics, the effectiveness of the insect repellent active ingredient can be adversely impacted. This is particularly so with respect to DEET, a preferred repellent active ingredient.

Moreover, it is desirable that, when a sunscreen preparation is applied to the skin, it forms a smooth, generally uniform, layer of sunscreen that is non-greasy and has other good cosmetic characteristics. This presents additional problems for a developer of sunscreens.

A need therefore exists for improved insect repellent sunscreens.

DISCLOSURE OF THE INVENTION

In one aspect, the invention provides an insect repellent sunscreen composition. There is between 10% and 40% by weight of sunscreen agent having absorption capability at least somewhere within the ultraviolet radiation range of 290 to 400 nm. There is also between 2% and 50% by weight of insect repellent (preferably less than 25%, even more preferably less than 10%), between 1% and 20% by weight of neopentanoate (preferably an alkyl, $C_{30}$ or less, neopentanoate such as octyldodecyl neopentanoate), between 20% and 60% by weight of water, and between 0.1% and 15% by weight of emulsifier (especially preferably anionic emulsifier). A water resistance agent can also be included, such as 0.01% to 5% by weight of a polymer of vinylpyrrolidone.

Octyldodecyl neopentanoate ($C_{25}H_{50}O_2$) is marketed as an emollient or skin softener by Bernel Chemical Company as ELEFAC I-205. Other known emollients can also be added, such as liquid esters, silicone fluids, mineral oil, allantoin, lanolin, petrolatum, vegetable oil such as jojoba oil and castor oil, propylene glycol, and fatty alcohols such as cetyl alcohol and stearyl alcohol.

The insect repellent is preferably selected from the group consisting of N,N-diethyl toluamide ("DEET"), N,N-diethyl benzamide, p-menthane-3,8-diol, 1S ,3S,4S,6R-carene-3, 4diol (Sumitomo-U.S. Pat. No. 5,130,136), 1-piperidinecarboxylic acid, 2-(2-hydroxyethyl)-, 1-methylpropylester, 1-(3-cyclohexen-1-ylcarbonyl)-2-methylpiperidine, 1-(3-cyclohexen-1-ylcarbonyl) piperidine, N,N-diethyl mandelamide, isopulegol hydrate, ethyl-3-[N-n-butyl-N-acetyl] aminopropionate, diisopropyladipate, alpha biasabal, spearmint oil, benzyl alcohol, N,N-diethylphenylacetamide, vitamin E, citronella oil, clove oil, coconut oil, cedar oil, geraniol, lemon grass oil, thyme oil, rosemary oil, mint oil, geranium oil, eugenol, 3-acetyl-2-(2-,6-dimethyl-5-heptenyl) oxazolidine, (2-hydroxymethylcyclohexyl) acetic acid lactone, and eucalyptol. If DEET is used, DEET is preferably in the 7.5% to 30% range. However, for certain environments, such as insect-infested swamps, even higher levels of DEET may be appropriate.

The sunscreen agent can be any agent approved for human skin application that has absorption capability somewhere from 290 to 400 nm. It is preferably selected from the group consisting of 2-ethylhexyl methoxycinnamate, 2-ethylhexyl salicylate, 2-ethylhexyl 2-cyano-3,-3-diphenylacrylate, oxybenzone, padimate O, and titanium dioxide. However, it may also include mixtures of those components and/or other sunscreens such as aminobenzoic acid; cinoxate; diethanolamine p-methoxycinnamate; digalloyl trioleate; dioxybenzone; ethyl 4-[bis(hydroxypropyl)] aminobenzoate; glyceryl p-aminobenzoate; homosalate; lawsone; menthyl anthranilate; 2-phenylbenzimidazole-5-sulfonic acid; red petrolatum; sulisobenzone; zinc oxide; and triethanolamine salicylate.

The water resistance agent is preferably a polymer of vinylpyrrolidone and, of such polymers, preferably is a copolymer of polyvinylpyrrolidone with long alkyl chain olefins (an "alkylated PVP"). See e.g. U.S. Pat. No. 4,810, 489. The most preferred water resistance agent is Ganex V-220, available from GAF Corporation. Ganex V-220 is 1-eicosene polymer with 1-ethenyl-2-pyrrolidinone. Other suitable water resistance agents are polyisobutene (Prisorine SQS3758, Unichema); tricontanyl PVP (Ganex WP-660-ISP); acrylates/octylacrylamide copolymer (Dermacryl-79; Versatyl-42; National Starch); dimethicone 350 cSt (Dow); PVP/hexadecene copolymer (Ganex V-216-ISP); Lexorez® 100 (Inolex); acrylates/$C_{10-30}$alkyl acrylate crosspolymer; and Pemulen TR1/TR2 (Goodrich).

Thickeners assist in achieving even better SPF protection, apparently by contributing to the protective film left on the skin when the sunscreen composition is applied, although the exact mechanism of the thickeners' contribution to SPF protection is not precisely known. Preferred thickeners are xanthan gum, guar gum, alginate gums, magnesium aluminum silicate, stearic acid, and cetyl alcohol. Other desirable thickeners are silicates and clays (e.g. bentonite, laponite), polymeric thickeners (such as Carbopol polymers from BF Goodrich), polyethylene glycol thickeners, cellulosic thickeners (such as hydroxyethylcellulose), fatty alcohols, and carbomers (such as CTFA).

The emulsifier is preferably an anionic surfactant such as Amphisol from Givaudan-Roure (diethanolamine-cetyl phosphate). However, a wide variety of other anionic surfactants appear useful for this purpose such as phosphate esters, phosphorous organic derivatives, sulfates of alcohols and ethoxylated alcohols, alkanolamides, sulfosuccinates, alkylaryl sulfonates, and other protein-based, fluorocarbon-based, and silicone-based surfactants.

If desired, other conventional sunscreen ingredients can also be added. These include silicone fluid (e.g. Dow Silicone 200-Dimethicone-a lubricity provider), glycerin (a film enhancer), Germaben II (a preservative), and a fragrance. 2-Ethylhexyl-2-cyano-3,3-disphenyl acrylate may also be added as an additional sunscreen agent. This material is available commercially from BASF as Octocrylene.

In another aspect, the invention provides a method of applying such compositions to an exposed portion of a human's body so that it functions both as a sunscreen and insect repellent. In another aspect, the invention provides methods of making such compositions.

The compositions of the present invention provide a high degree of SPF protection even after exposure to water. Yet they also have exceptional insect repellent capability. The above compositions are particularly designed to have an SPF value ("Sun Protection Factor") in the "Standard Test" (described below) of at least SPF 15. This "Standard Test" is a test without the water resistance challenge. However, as noted below, a similar test can be conducted which also includes challenge by immersion.

"SPF 15" is colloquially understood to mean, for example, that if one burns in the sun after 10 minutes with no sunscreen, it will take fifteen times longer to burn equivalently when the product is applied as directed. However, for purposes of the present patent, SPF 15 (and SPF) are more precisely defined in accordance with the "Standard Test". This Standard Test is generally in accordance with the "Proposed Monograph for OTC Sunscreen Drug Products" issued by the Food and Drug Administration, Aug. 25, 1978, Federal Register Volume 43, Number 166, 38206–38269.

The light source used for the test is the Solar Ultraviolet Simulator, Model 10S, made by Solar Light Company, consisting of a 150 watt xenon arc lamp together with all required optical elements and a regulated power supply. Test panels consist of twenty male and female subjects with inclusion/exclusion criteria as per the above-cited FDA Proposed Monograph. A physical examination is made to determine the presence of sunburn, suntan, scars, active dermal lesions, and/or uneven skin tones on the areas of the backs to be tested. The presence of nevl, blemishes, or moles will be acceptable if they will not interfere with the study results. Excess hair on the back is shaved.

A control compound is 8% homosalate (HMS). Each test site area serves as an area for determining the subject's minimal erythema dose (MED) after application of either the sunscreen products, the 8% HMS control, or for determining the subject's MED when the skin is unprotected. The MED is the time of exposure that produces minimally perceptible erythema at 16 hours post-exposure. The area to be tested is the back between the belt line and the shoulder blades (scapulae) and lateral to the midline. The test site areas are preferably square.

Each test site area for applying a product or standard control is 50 cm sq. These test sites are outlined while the person to be tested is in an upright position, the position in which irradiation will take place. Each test site area for the test material and the 8% HMS is divided into 1 cm sq test areas.

To insure standardized reporting and to define a product's SPF value, the application of the product is expressed on a weight basis per unit area which establishes a standard film. The test sunscreen product application is 2 mg/cm sq, as is the 8% HMS control.

For cremes, heavy gels, and butters, the product is warmed slightly so that it can be applied volumetrically. During such heating, care is taken so as not to alter the product's physical characteristics. Pastes and ointments are weighed, then applied by spreading on the test site.

Before exposing the test site areas to ultraviolet irradiation and after applying a product, a waiting period of 15 minutes is employed. Then a series of UV light exposures (units of time) are administered to the subsites on each subject with the solar simulator.

One series of exposures is administered to the untreated, unprotected skin to determine the MED. The MED of the subject's unprotected skin is determined on the test day. The protected test sites (8% HMS control and/or test sunscreen product) are also exposed to UV light.

The time intervals selected are a geometric series represented by $(1.25)n$, wherein each exposure time interval is 25 percent greater than the previous time. The value of the third subsite is the expected SPF value multiplied by the MED. The SPF is then reported as the MED of the protected skin divided by the MED of the unprotected skin.

Similar testing can be performed to evaluate the water resistance SPF. For this purpose the subjects having the sunscreen and control are exposed to 80 minutes of water immersion in a whirlpool prior to UV exposure. The 80 minutes are broken up into four 20 minute exposures, each exposure being separated by a 20 minute rest period. The person's back is then air dried prior to exposure to the UV light.

The objects of the present invention therefore include providing compositions of the above type:

(a) which have both high SPF protection and good insect repellent characteristics;

(b) which have good water resistance SPF characteristics;

(c) which have desirable cosmetic characteristics, particularly with respect to skin softening; and (d) which have a non-greasy feel.

These and still other objects of the present invention (e.g., methods for making and using these compositions) will be apparent from the description which follows. The following description is merely of the preferred embodiments. Thus, the claims should be looked to in order to understand the full scope of the invention.

BEST MODES FOR CARRYING OUT THE INVENTION

The following are example compositions of the present invention. The numbers listed below are weight percentages.

| Material | A | B | C | D | E |
|---|---|---|---|---|---|
| Stearic Acid (Emersol 132) | 5.00 | 4.00 | 5.00 | 4.00 | 5.00 |
| Cetyl Alcohol | 2.00 | 1.60 | 2.00 | 1.60 | 2.00 |
| Amphisol (DEA-Cetyl Phosphate) | 2.00 | 2.00 | 2.00 | 2.00 | 2.00 |
| Dow Silicone 200 (100 cps) (Dimethicone) | 0.50 | 0.50 | 0.50 | 0.50 | 0.50 |
| Octyl Methoxycinnamate | 7.50 | 7.50 | 7.50 | 7.50 | 7.50 |
| Octyldodecyl Neopentanoate (Elefac I-205) | 10.00 | 10.00 | 10.00 | 10.00 | 10.00 |
| Octyl Salicylate | 5.00 | 5.00 | 5.00 | 5.00 | 5.00 |
| Benzophenone-3 | 5.00 | 5.00 | 5.00 | 5.00 | 5.00 |
| DEET | 7.50 | 20.00 | 7.50 | 25.00 | 7.50 |
| Deionized Water | 47.20 | 40.10 | 49.20 | 34.60 | 40.20 |
| Magnesium Aluminum Silicate (Veegum) | 0.75 | 0.75 | 0.75 | 0.75 | 0.75 |
| Xanthan Gum (Keltrol by Kelco) | 0.25 | 0.25 | 0.25 | 0.25 | 0.25 |
| Germaben IIE (preservative) | 1.00 | 1.00 | 1.00 | 1.00 | 1.00 |
| Ganex V-220 | 2.00 | 2.00 | 2.00 | 2.50 | 2.00 |
| Glycerin | 4.00 | | | | 4.00 |
| Fragrance | 0.30 | 0.30 | 0.30 | 0.30 | 0.30 |
| Ultra Fine TiO$_2$ (Cardre) | | | 2.00 | | 2.00 |
| Octocrylene | | | | | 2.00 |
| | 100.00 | 100.00 | 100.00 | 100.00 | 100.00 |

As noted below, in comparative tests of the 7.5% DEET compositions listed above with a 10% DEET SPF 15 "Sunsect" commercial, competitive sunscreen/repellent product, Formulas A and C had better biting protection than the Sunsect 10% composition, notwithstanding the use of lower DEET levels. In another competitive test, Formula B was compared to a 20% DEET Sunsect combined repellent and sunscreen. Again, the present invention provided better insect protection than the competitive product.

The insect protection tests were "arm in a cage" type tests. In these tests, human subjects first washed their arms with soap and then rinsed and dried their arms. They then treated their forearms with similar amounts of the products, put on white cotton gloves, and then exposed their forearms to insects confined within insect cages. The cages had the types and numbers of insects described below. The results of these experiments are detailed below.

SAMPLE

| | MOSQUITO DENSITY | REPS | Adjusted* Protection Time In Hours FIRST BITE |
|---|---|---|---|
| A 7.5% DEET | 200 | 6 | 3.6 |
| C 7.5% DEET | 200 | 6 | 2.6 |
| Sunsect 10% DEET | 200 | 6 | 2.4 |

| | MOSQUITO DENSITY | Reps | Mean Protection Time In Hours First Bite |
|---|---|---|---|
| B 20% DEET | 1000 | 6 | 5.3 |
| Sunsect 20% DEET | 1000 | 6 | 4.2 |

| | STABLE FLY DENSITY | Reps | Mean Protection Time In Hours First Bite |
|---|---|---|---|
| B 20% DEET | 3000 | 6 | 0.9 |
| Sunsect 20% DEET | 3000 | 6 | 0.7 |

*For testing over three days.

The compositions of the present invention had a static (no water challenge) SPF of at least 15 (using tests essentially the same as the Standard Test) and also retained good SPF protection after exposure to water. Formula A had a static SPF of 16.3 and a water resistance SPF of 15.8. Formula B had a static SPF of 16.2 and a water resistance SPF of 14.7. Formula C had a static SPF of 26.3 and a water resistance SPF of 24.6. Formula D had a static SPF of 16.5 and a water resistance SPF of 15.8. Formula E had a static SPF of 34.5 and a water resistance SPF of 31.8.

To manufacture the preferred compositions, one preferably combines the components except the water, glycerin, Veegum, Keltrol, perfume, and Germaben in a first kettle and heats them to 180° F. for about 15 minutes until a clear yellow liquid is achieved.

In a second kettle the glycerin and water are mixed and heated to 160° F. One can then separately prepare a dry mix of the Veegum and Keltrol. This is slowly added to the second, glycerin kettle while mixing with a high shear. One agitates the mixture until hydration is complete, the mix is thickened, and the mix is free of lumps. This typically takes about 15 minutes at 160° F.

The temperature is then increased to 175° F. in the second, glycerin kettle. The contents of the first kettle are mixed with it, and the mixture is agitated for 15 minutes. One then quench cools the mixture to 110° F. and adds the Germaben and perfume. This mixture is agitated for 30 minutes and then cooled to room temperature.

The preferred compositions can be squeezed, poured, or otherwise applied onto human skin and then rubbed on and spread out over the skin. This preferably takes place a few minutes prior to sun exposure.

It should be noted that what has been described above are merely the preferred embodiments of the present invention. Many other embodiments are possible within the scope of the claims. Thus, the claims should be looked to in order to judge the full scope of the invention.

INDUSTRIAL APPLICABILITY

The invention provides sunscreens having superior insect repellent capability even when using lower levels of the repellent active ingredient than in comparable competitive products. It appears to be especially useful for protecting human skin during swimming or sunbathing outdoors.

I claim:

1. An insect repellent sunscreen composition, comprising:
   a. between 10% and 40% by weight of organic sunscreen agent having absorption capability at least somewhere within the ultraviolet radiation range of 290 to 400 nm;
   b. between 2% and 50% by weight of insect repellent;
   c. between 1% and 20% by weight of neopentanoate;
   d. between 20% and 60% by weight of water; and
   e. between 1% and 15% by weight of emulsifier.

2. The insect repellent sunscreen composition of claim 1, wherein the emulsifier is an anionic emulsifier.

3. The insect repellent sunscreen composition of claim 2, wherein the neopentanoate is alkyl neopentanoate.

4. The insect repellent sunscreen composition of claim 2, wherein the neopentanoate is octyldodecyl neopentanoate.

5. The insect repellent sunscreen composition of claim 2, further comprising a water resistance agent.

6. The insect repellent sunscreen composition of claim 2, further comprising a water resistance agent which is a polymer of vinylpyrrolidone.

7. The insect repellent sunscreen composition of claim 6, wherein the water resistance agent is a polymer of vinylpyrrolidone which is between 0.01% and 5% by weight of the composition.

8. The insect repellent sunscreen composition of claim 7, wherein the water resistance agent is a copolymer of polyvinylpyrrolidone and an olefin.

9. The insect repellent sunscreen composition of claim 2, wherein the composition has an SPF value in the "Standard Test" of at least SPF 15.

10. The insect repellent sunscreen composition of claim 2, wherein the insect repellent is selected from the group consisting of N,N-diethyl toluamide ("DEET"), N,N-diethyl benzamide, p-menthane-3,8-diol, 1-piperidinecarboxylic acid, 2-(2-hydroxyethyl)-,1-methylpropylester, 1-(3-cyclohexen-1-ylcarbonyl)-2-methylpiperidine, citronella oil, clove oil, coconut oil, cedar oil, geraniol, lemon grass oil, thyme oil, rosemary oil, mint oil, geranium oil, and eugenol.

11. The insect repellent sunscreen composition of claim 10, wherein the insect repellent is N,N-diethyl toluamide.

12. The insect repellent sunscreen composition of claim 2, wherein the sunscreen agent is selected from the group consisting of 2-ethylhexyl methoxycinnamate, 2-ethylhexyl salicylate, 2-ethylhexyl 2-cyano-3,-3-diphenylacrylate, oxybenzone, padimate O, and titanium dioxide.

13. The insect repellent sunscreen composition of claim 12, wherein the sunscreen agent is a mixture of 2-ethylhexyl methoxycinnamate, 2-ethylhexyl salicylate, and oxybenzone.

14. The insect repellent sunscreen composition of claim 2, further comprising a thickener selected from the group consisting of xanthan gum, guar gum, alginate gums, magnesium aluminum silicate, stearic acid, and cetyl alcohol.

15. The insect repellent sunscreen composition of claim 14, further comprising silicone fluid and a fragrance.

16. A method of applying a composition to an exposed portion of a person's body so that the composition functions as a sunscreen and insect repellent, comprising the step of applying the claim 1 composition to external human skin.

17. A method of making a composition that is both a sunscreen and an insect repellent, comprising mixing the sunscreen agent, insect repellent, neopentanoate and emulsifier of claim 1 with water so as to yield the claim 1 composition.

* * * * *

UNITED STATES PATENT AND TRADEMARK OFFICE
CERTIFICATE OF CORRECTION

PATENT NO. : 5,716,602
DATED : February 10, 1998
INVENTOR(S) : Heidi J. Uick

It is certified that error appears in the above-identified patent and that said Letters Patent is hereby corrected as shown below:

At. col. 7, line 10, please change "1%" to —0.1%—.

Signed and Sealed this

Fifteenth Day of February, 2000

Attest:

Q. TODD DICKINSON

Attesting Officer

Commissioner of Patents and Trademarks